United States Patent
Shah et al.

[11] Patent Number: 5,922,342
[45] Date of Patent: Jul. 13, 1999

[54] LATERAL EDGE COATED CONTROLLED RELEASE PHARMACEUTICAL COMPOSITIONS

[75] Inventors: Ashok Chandulal Shah, Kalamazoo; Nancy J. Britten, Portage, both of Mich.

[73] Assignee: Pharmacia & Upjohn Company, Kalamazoo, Mich.

[21] Appl. No.: 08/391,825

[22] Filed: Feb. 21, 1995

Related U.S. Application Data

[63] Continuation of application No. 08/090,101, May 15, 1993, abandoned, which is a continuation of application No. PCT/US91/05572, Aug. 13, 1991, which is a continuation of application No. 07/591,098, Oct. 1, 1990, abandoned.

[51] Int. Cl.[6] .................................................. A23K 1/18
[52] U.S. Cl. ........................ 424/438; 424/464; 424/474; 424/475; 424/479; 424/480
[58] Field of Search ..................................... 424/438, 464, 424/474, 475, 479, 480

[56] References Cited

U.S. PATENT DOCUMENTS

| | | | |
|---|---|---|---|
| 4,723,958 | 2/1988 | Pope | 604/890.1 |
| 4,786,501 | 11/1988 | Janski | 424/422 |
| 4,863,455 | 9/1989 | Whitehead | 604/890.1 |
| 4,898,733 | 2/1990 | DePrince | 424/425 |
| 5,002,772 | 3/1991 | Curatolo | 424/438 |
| 5,004,614 | 4/1991 | Staniforth | 424/466 |

*Primary Examiner*—D. Gabrielle Brouillette
*Attorney, Agent, or Firm*—William G. Jameson

[57] ABSTRACT

The invention provides a controlled release composition comprising a compressed core containing a drug having two parallel planar surfaces (i.e. the top and bottom), and a seal coating surrounding the core except on said planar surfaces (i.e. on all lateral surfaces). The seal coating comprises a film coating of an impermeable material.

10 Claims, 2 Drawing Sheets

LATERAL EDGE COATED CONTROLLED RELEASE PHARMACEUTICAL COMPOSITIONS

The present application is a continuation application of U.S. Ser. No. 08/090,101, filed May 15, 1993, now abandoned, which is a continuation of International Patent Application PCT/US91/05572, filed Aug. 13, 1991; which is a continuation of U.S. Ser. No. 07/591,098, filed Oct. 1, 1990, abandoned.

BACKGROUND OF THE INVENTION

1. Field of the Invention

This invention relates to controlled release drug delivery system which provides constant release of therapeutic agent by maintaining a constant surface area. Oral controlled release delivery, rumen bolus, sublingual, and buccal applications are indicated for a broad spectrum of drugs.

2. Description of Related Art

A number of devices have been developed for the sustained release of active medicament. Monolithic systems, where the drug is dispersed in a polymer matrix that is permeable to the drug, have been appealing because of their ease of manufacture. U.S. Pat. No. 4,369,172; U.S. Pat. No. 3,870,790; U.S. Pat. No. 4,357,469; U.S. Pat. No. 4,226,849; U.S. Pat. No. 3,590,117; U.S. Pat. No. 4,389,393; G.B. 2 053 682; U.S. Pat. No. 4,309,405; U.S. Pat. No. 4,309,406; U.S. Pat. No. 4,167,558; U.S. Pat. No. 4,259,314; and U.S. Pat. No. 3,065,143 are a few of the many examples in this category. U.S. Pat. No. 3,402,240; U.S. Pat. No. 3,062,720, and U.S. Pat. No. 3,456,049 represent sustained release tablets in which the drug is imbedded in an insoluble matrix. Drug release rates from these types of monolithic devices generally decline with time (T. Higuchi, J. Pharm. Sci., 50,874 (1961); T. J. Roseman, J. Pharm. Sci., 61,46 (1972); and H. K. Lonsdale, R. W. Baker, "Controlled Release of Biologically Active Agents", Ed. A. C. Tanquary, Plenum Press, N.Y. (1974)). These delivery systems also require relatively large amounts of excipients to maintain tablet integrity and produce the desired drug release rate. An Alza device, U.S. Pat. No. 3,926,188, consisting of a three layer laminate drug dispenser with a core of crystalline drug of low water solubility dispersed in homogeneous polymer matrix, also has a permeable rate controlling polymer coating. Medicament is not released at a constant rate, instead dissolution profiles show a strong initial burst effect, which may lead to toxicity with many drugs.

One of the major goals of formulators of sustained release pharmaceuticals has long been to provide an approximately constant rate of drug release over an extended period of time. European Patent Application 84401152.8 (Publication No. 0 131 485); Derwent 85-019972/04) claims to have achieved constant drug release by a controlled surface erosion mechanism. This rather cumbersome, multi-component oral delivery system includes: 1) 10–90% drug (with water solubility of 1/5 to 1/1000); 2) 1–40% surface controlling compound; 3) 0.05–1% surface activator; 4) 0.1–2% surfactant. Tablets are either spherical or have a thickness/diameter ratio that permits tablet erosion and penetrant control sufficient for controlled surface erosion.

A second method for generating zero-order release is to maintain a constant tablet surface area, available for dissolution. UK Patent Application GB 2 078 518 (Derwent 85413 D/47); U.S. Pat. No. 4,465,660 (Derwent 84-218985/35); and U.S. Pat. No. 4,547,358 (Derwent 88-355419/50) detail oral drug delivery systems specifically for theophylline. The tablets are uncoated, non-disintegrating, have flat surface, and contain 94.8–99% theophylline. "Relatively steady" release rates are obtained by severely restricting tablet thickness to 0.08–0.12 in. Constant release, however, is not maintained since the surface area of the tablet decreases with time.

Another technique of producing constant release of therapeutic agent utilizes one or more apertures extending partially or completely through the tablet. U.S. Pat. No. 3,113,076; U.S. Pat. No. 4,217,898; U.S. Pat. No. 3,146,169; G.B. 1 372 040; and U.S. Pat. No. 4,218,433 exemplify this type of delivery system. As the outer surface area of these tablets decreases with time, the surface area created by the dissolving aperture(s) increases, keeping the total tablet surface area fairly constant. Others have tried to achieve constant release rates by covering the tablet partially or totally with slowly dissolving materials. Japanese patent J6 2053 918 (Derwent 87-105812/15) claims a sustained release tablet with a core of disintegrating substance (that is harmful to the stomach and has a bad taste) buried completely in the inner core of the tablet, which has a thickness twice or less the thickness of the outer part of the tablet. Uniform drug release rates are not obtained. Constant medicament surface area is maintained in J6 1243016 Derwent 86-328111/50), by the use of a ring core of active substance and an outer ring portion that dissolves at the same slow rate as the inner drug core specified to be twice the outer ring width. Broad application of this system would prove to be difficult and time consuming, attempting to match polymer dissolution rates to each drug used.

Australian Patent Application 27462/63 (Derwent 12045) relates to anti-aphthous preparations and describes a vaccine implant device having an oblong body that is protected by a moisture-repelling surface layer except at one end or at both ends. The vaccine substance (in powdered form) is homogeneously mixed with a finely divided inert resorbable vehicle (for example, cholesterol, stearic acid or zinc oxide), compressed and coated (except at free access surfaces) so that it is gradually reabsorbed together with the other components of the body from the moment of its implantation in an animal until its complete reabsorption. It is disclosed that this period of time may be extended to three to five years.

European Patent Application 88304974.4 (Publication No. 0 294 993) describes a controlled drug delivery system which comprises one or more active substances homogeneously dispersed, with or without inert excipients, and contained substantially in the space of a tablet or bolus by means of an all-covering essentially impermeable wall or coating (for example ethylene-vinyl acetate) except for one or more strips of removed wall or coating from the side of said devices. A substantially constant rate (i.e. zero-order) of release is disclosed. The surface area available for dissolution does not necessarily remain constant since the bolus can have inert or dissolvable ingredients. Since only a minute portion of the surface is available for dissolution, release rates are very slow (the fastest shown was 70% dissolved in 35 days). The application of this system to most conventional oral sustained release formulations would be impossible.

SUMMARY OF THE INVENTION

According to the present invention, a controlled release composition is provided comprising a compressed core containing a drug having two parallel planar surfaces (i.e. the top and bottom), and an impermeable coating surrounding the core except on said planar surfaces (i.e. on all lateral surfaces). The impermeable coating may comprise a film coating of an impermeable material.

The compressed core consists of at least 90% of non-disintegrating therapeutic agent(s) compressed into a solid dosage form. The remaining 0 to 10% of the compressed core may contain non-disintegrating ingredients that are conventional in tablet making such as binders, lubricants, compression aids, flow aids and the like. Thus, the core is free of materials that cause swelling (i.e. cellulose derivative of the monocrystalline or cross-linked types or other polymeric substances) or disintegration (i.e. resins, corn starch, starch derivatives and the like).

DETAILED DESCRIPTION OF THE INVENTION

The major objective of the present invention is to provide a multi-purpose controlled release dosage form that produces a constant rate of drug release, is easy to manufacture, cost effective, and feasible for a wide range of medications. Uniform release rates are achieved by utilizing unique designs in which the surface area available for dissolution, remains constant with time.

The controlled release dosage forms of this invention comprise a compressed core containing therapeutic agent(s) and having two parallel planar surfaces (i.e. the top and bottom), and an impermeable seal coating on surfaces except said planar surfaces (i.e. all lateral surfaces).

The simplicity of design of the controlled release compositions of the present invention make it useful for a wide range of applications, including oral controlled release formulations, rumen boluses, and bioadhesive sublingual and buccal dosage forms.

The compressed core may be of various shapes, including circular, triangular, elliptical, hexagonal, etc., provided the core has two parallel planar surfaces (usually easily identified as the top and bottom surfaces).

Certain additional components may be introduced depending on the functional requirements imposed by the dosage form's intended use. A rumen bolus, for example, could incorporate, in the core of the device, a bar, plate, or layer of metal or other comparably dense substance, to assure retention of the bolus in the rumen. Optionally, depending on the desired specific gravity of the device, materials of sufficiently dense composition may be dispersed throughout the bolus and/or the impermeable edge seal coating. Similarly, a bioadhesive layer may be affixed to one of the parallel surfaces of an edge coated buccal or sublingual tablet of this invention, in order to secure it to the lining of the mouth. An alternative method of preparing such a device, still embodying the present invention, would be to admix the drug with a bioadhesive polymer prior to compression and edge coating.

It is another objective of this invention to provide a delivery system which allows constant release of drugs with high dose requirements. Some medications must be administered in dosages up to 1500 mg. Clearly, the incorporation of excipients, essential for matrix type systems, would make the tablet so large that it would be unswallowable.

Figure 1:
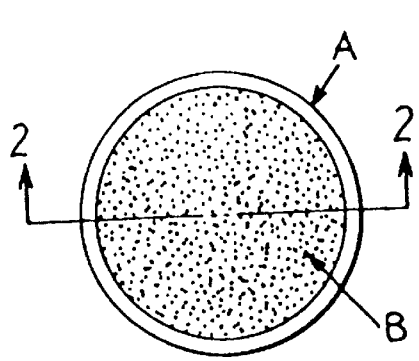
FIGS. 1A and 2, respectively, illustrate a top and perspective view of a controlled release composition of the present invention, with circular shape and parallel planar surfaces.
FIG. 1B is a sectional view taken along the line 1A–1B in FIG. 1A. Impermeable seal coating A, covers the lateral tablet edge. Therapeutic agent(s) is released from the two planar surfaces, B and b.
Figure 2:
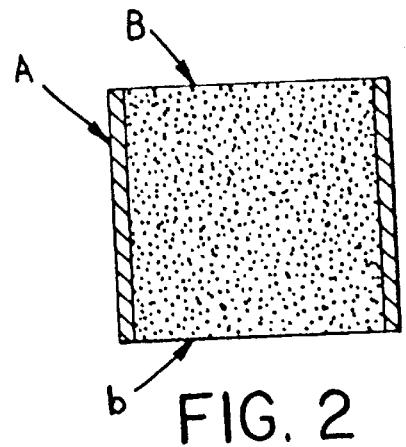
Figure 3:
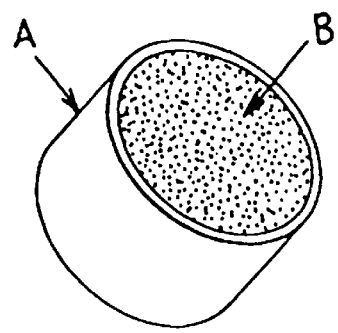
FIG. 3 is a representation of the tablet of FIGS. 1A and 2, after some dissolution of the therapeutic agent has occurred. The impermeable seal coating remains intact, while dissolution has reduced the thickness of the core. The total tablet surface area is kept constant until dissolution is complete, thus providing a constant drug release.
Figure 4:
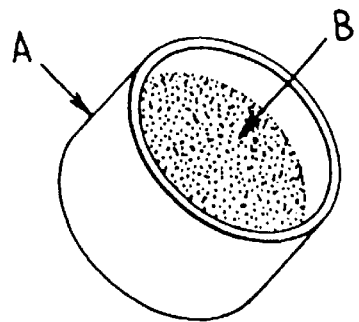
FIG. 4B and 4A, respectively, depicts the top and perspective views of an edge coated triangular rumen bolus of the present invention, having two planar surfaces (top planar surface labeled B).
FIG. 4C is a sectional view taken along the line 4C—4C in FIG. 4B. As seen in the cross section FIG. 4C, a metal bar or plate (X) is imbedded in the core to retain the bolus in the rumen.
Figure 5:
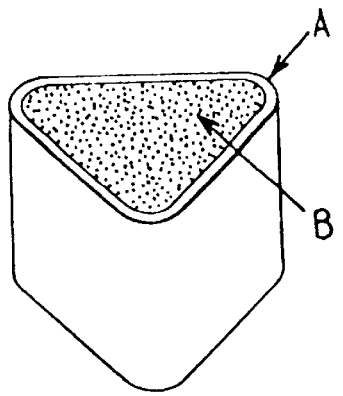
FIGS. 5B and 5A, respectively, depicts the top and perspective views of an edge coated buccal delivery system. Impermeable seal coating (A) covers the lateral tablet surfaces.
FIG. 5C is a sectional view taken along the line 5C—5C in FIG. 5B. A bioadhesive is applied to the bottom planar surface (b) to bond the composition to the mouth lining. Drug dissolution occurs from the top planar surface (B) at a constant rate, since the surface area available for dissolution is unchanged.
Figure 6:
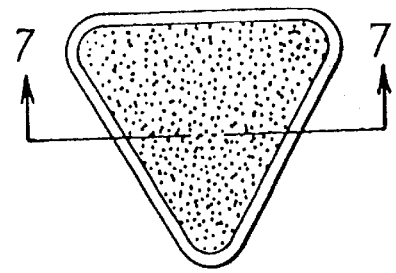
Figure 7:
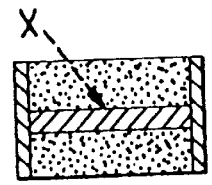
Figure 8:
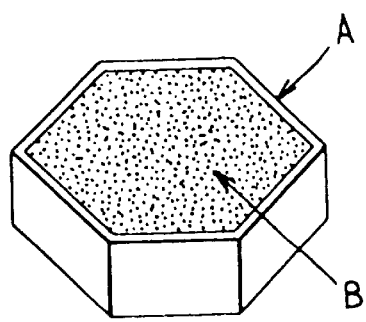
Figure 9:
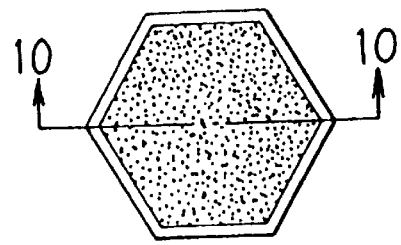
Figure 10:
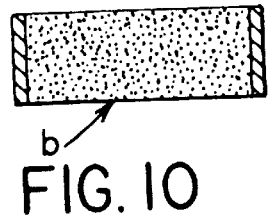

The core formulation, in addition to the therapeutic agent (s) for which controlled release is desired, can contain up to about 10% w/w of soluble or insoluble inert ingredients, other than disintegrating agents (like starch swellable polymers, alginates, etc.), that are conventional in tablet making, such as magnesium stearate; stearic acid; colloidal silicone dioxide; talc; titanium dioxide; magnesium, calcium, and aluminum salts; lactose; povidone; high molecular weight polyethylene glycols and derivatives; bio-erodible polymers such as poly(orthoesters) and polyanhydrides and anhydride co-polymers; polyoxystearates; carboxymethyl cellulose; cellulose ethers such as acetate phthalate, acetate succinate, and cellulose acetate N,N-diethylamino acetate; polyvinyl alcohol; and the like. For rumen boluses the core formulation may contain up to 50% w/w of non-disintegrating pharmaceutically acceptable ingredients, as increased size of the device may be necessary for retention in the rumen.

The therapeutic agent is non-disintegrating and comprises at least 90% w/w of the core oral controlled release, buccal, or sublingual formulation. The core formulation contains at least 20 mg of therapeutic agent.

Any therapeutic agent that is non-disintegrating, i.e. one that does not alter the dissolving surface by swelling, and lends itself to controlled release administration can be utilized in the present invention, including such agents such as antihistamines, laxatives, vitamins, decongestants, gastrointestinal sedatives, antacids, anti-inflammatory substances, antimanics, anti-infectives, coronary vasodilators, peripheral vasodilators, cerebral vasodilators, psychotropics, stimulants, antidiarrheal preparations, antianginal drugs, vasoconstrictors, anticoagulants, antirombotic drugs, analgesics, antipyretics, hypnotics, sedatives, antiemetics, antinauseants, anticonvulsants, neuromuscular drugs, hyperglycemic and hypoglycemic agents, thyroid and antithyroid preparations, diuretics, antispasmodics, uterine relaxants, mineral and nutritional additives, antiobesity drugs, hormones, anthelmentics, and such other agents that may be desired.

For oral controlled release delivery systems, where constant release is desired, the therapeutic agent should be limited to drugs which to a large extent (greater than 90%) will not ionize in the physiological pH of the gastrointestinal tract. Drugs which ionize readily may be used in designs of the present invention if they are admixed with an appropriate buffering agent, such that the pH at the dissolving surface is maintained. In such cases the drug and buffering agent will comprise at least 90% of the core formulation. Buffering agents may include, but are not limited to carboxylic acid, citrate, phosphate, and TRIS buffers.

For rumen boluses and controlled release compositions for bioadhesive sublingual or buccal administration, no limitation on the degree of ionization is required.

The amount of therapeutic agent contained in the controlled release compositions of this invention will vary depending on the drug or drugs employed.

The therapeutic agent contained in the controlled release composition(s) of this invention are released at a substantially constant rate (i.e. zero order) over an extended period of time. For example, in oral tablets the therapeutic agent is released over a period of 6 to 24 hours, in sublingual (or buccal) tablets the therapeutic agent is released over a period of 3 to 12 hours, in rumen boluses the therapeutic agent is released over a period of 1 to 365 days.

The impermeable seal coating is selected from one or more of those film forming materials which is capable of substantially, protecting the non-coated surfaces of the core from dissolution. Accordingly, the coating material may be polyvinylchloride, polyvinyl acetate, ethyl cellulose, polyurethanes, cellulose acetate, poly(alkyl methacrylate), cellulose ethers or another impermeable seal substance.

The amount of seal coating necessary for protecting the core will vary depending on the surface area of the lateral surfaces of the core and the efficiency of the coating equipment and operation.

The impermeable seal coating may be applied by various means well known to those skilled in the art. The preferred method of coating utilizes a modified Elanco hard gelatin capsule sealing machine. The tablet is held in place on the two parallel planar surfaces. A coating wheel with an enlarged groove is run through a pan containing a solution or suspension of coating material. The coating material is picked up in the groove and applied to the lateral edges of the rotating tablet as the wheel circumscribes the tablet. Another approach that can be used is to roll the tablets in a narrow trough, over a moving belt covered with wetted coating material. A final drying step would be necessary. A modified tablet printing machine can also be used to apply the seal coating. A number of other methodologies may be applicable for the coating of tablets of this invention.

Dense filler materials, that may be incorporated into a rumen bolus of the present invention include, but are not limited to, iron ores, iron powder, iron alloy coated epoxy, iron-magnesium alloy, aluminum powder, aluminum flake, steel, non-swellable cross-linked organic polymers, zinc, zinc alloy, ground mica, and other minerals, Bioadhesive agents, which may be used in sublingual and buccal formulations of the present invention include, but are not limited to, hydroxypropyl cellulose, carboxypolymethylene, carboxymethyl cellulose, poly (methyl methacrylate).

In order that the invention may be more fully understood it will now be described in more detail, though only by way of illustration, with reference to the following examples.

Example 1

Edge Coated Salicylic Acid Tablets 400 mg Salicylic Acid Powder is compressed at 2500 psi for 30 seconds, on a Carver Press, with a conventional circular flat tablet die with a diameter 1.033 cm. The tablet edges are hand coated (by brush) with a 20% w/w solution of polyvinylchloride in tetrahydrofuran (THF). An edged coated tablet is compared to an uncoated tablet for release rate comparison in an automated spin-filter dissolution apparatus and the dissolved drug analyzed by spectral analysis.

Dissolution Conditions

Media: 1000 ml of distilled water; temperature: 37° C.; stirring speed: 300 rpm; sampling interval: 10 min.

Table 1 lists the percent dissolved per hour and the rate of dissolution for the edge coated tablet of the present invention and an uncoated tablet. The edge coated salicylic acid tablet produced essentially constant drug release for 13 hours, while a continuously declining rate of release was exhibited by the uncoated tablet.

Example 2

Edge Coated Salicylic Acid/Buffering Agent Tablets

Sufficient amounts of Salicylic Acid Powder and Citric Acid Powder are mixed in a 1:1 ratio, to produce a uniform batch of tablets. The mixture is compressed on a conventional tableting machine, using a circular flat tablet die with a diameter of 1.033 cm. Each tablet core contains 300 mg of Salicylic Acid, 300 mg Citric Acid. Tablet edges are coated with polyvinyl chloride, using a modified hard gelatin capsule sealing machine.

Example 3

Edge Coated MGA Rumen Bolus

Sufficient amounts of melengestrol acetate and polyethylene glycol 6000 are mixed in a 1:1 ratio, to produce a uniform batch of boluses. The mixture is compressed around a metal plate (which will be in the center core of the bolus). Each bolus contains 50 mg of melengestrol acetate. Bolus edges are coated with cellulose acetate.

TABLE 1

| Time | EDGE COATED TABLET | | UNCOATED TABLET | |
| --- | --- | --- | --- | --- |
| (Hr) | % Dissolved | Rate* | % Dissolved | Rate* |
| 1 | 6.37 | 6.37 | 19.29 | 19.29 |
| 2 | 13.45 | 7.08 | 35.48 | 16.19 |
| 3 | 21.31 | 7.86 | 49.31 | 13.83 |
| 4 | 29.13 | 7.82 | 61.08 | 11.77 |
| 5 | 37.14 | 8.01 | 70.91 | 9.83 |
| 6 | 45.04 | 7.90 | 78.99 | 8.08 |
| 7 | 52.66 | 7.62 | 85.57 | 6.58 |
| 8 | 59.89 | 7.23 | 90.84 | 5.27 |
| 9 | 66.66 | 6.77 | 94.64 | 3.80 |
| 10 | 72.96 | 6.30 | 96.65 | 2.10 |
| 11 | 79.20 | 6.24 | 97.09 | 0.44 |
| 12 | 86.15 | 6.95 | 97.09 | 0 |
| 13 | 91.59 | 5.44 | 97.09 | 0 |

*Percent dissolved per hour

We claim:

1. A tablet containing a non-disintegrating therapeutic agent that is released at a substantially constant rate on oral, sublingual or buccal administration to a mammal, the tablet comprising a compressed core containing at least 90% of the therapeutic agent and having two parallel planar surfaces, and an impermeable seal coating surrounding the core except on the planar surfaces and bearing no retention arms.

2. A tablet according to claim 1, which additionally comprises a bioadhesive layer affixed to one of the planar surfaces.

3. A tablet according to claim 1, which additionally comprises a bioadhesive polymer, obtainable by mixing the therapeutic agent with the bioadhesive polymer prior to compression and edge-coating.

4. A tablet according to any preceding claim, wherein the coating is selected from polyvinyl chloride, polyvinyl acetate, ethylcellulose, a polyurethane, cellulose acetate, a polyalkyl methacrylate or a cellulose ether.

5. A bolus containing a non-disintegrating therapeutic agent or nutrient that is released at a substantially constant rate on administration into the rumen or reticulum of a ruminant animal, the bolus comprising a compressed core containing at least 50% of the therapeutic agent or nutrient, and having two parallel planar surfaces, and an impermeable seal coating surrounding the core except at the planar surfaces and bearing no retention arms.

6. A bolus according to claim 5, wherein the core additionally contains a buffering agent.

7. A bolus according to claim 5 or claim 6, which additionally includes a bar, plate, layer or dispersion of a dense substance incorporated into the compressed core.

8. A tablet according to claim 1 wherein a buffering agent is incorporated into the compressed core.

9. A tablet for oral, sublingual or buccal administration to a mammal which releases therapeutic agent at a substantially constant rate, comprising a compressed core containing at least 90% of a non-disintegrating therapeutic agent and a buffering agent and having two parallel planar surfaces, an impermeable seal coating surrounding the core except on said planar surfaces and bearing no retention arms.

10. A bolus according to any of claims 5 to 7, wherein the coating is selceted from polyvinyl chloride, polyvinyl acetate. ethylcellulose, a polyurethane, cellulose acetate, a polyalkyl methacrylate or a cellulose ether.

* * * * *